United States Patent

Regan

[11] Patent Number: 5,888,185
[45] Date of Patent: Mar. 30, 1999

[54] EQUINE THERAPEUTIC DEVICE

[75] Inventor: Michael T. Regan, Ada, Okla.

[73] Assignee: Sports Prescriptions, Inc., Red Bluff, Calif.

[21] Appl. No.: 980,712

[22] Filed: Dec. 1, 1997

Related U.S. Application Data

[63] Continuation-in-part of Ser. No. 870,226, Jun. 6, 1997.

[51] Int. Cl.$^6$ ................................................ A61B 17/52
[52] U.S. Cl. .............................. 600/15; 600/9; 607/104
[58] Field of Search ........................................... 600/9, 15

[56] References Cited

U.S. PATENT DOCUMENTS

| | | |
|---|---|---|
| 3,905,367 | 9/1975 | Dapcich . |
| 4,026,299 | 5/1977 | Sauder . |
| 5,389,061 | 2/1995 | Nor .............................................. 600/15 |
| 5,426,925 | 6/1995 | Smargiassi ................................. 54/79.1 |
| 5,496,358 | 3/1996 | Rosenwald ................................ 607/108 |
| 5,507,792 | 4/1996 | Mason et al. ............................. 607/104 |
| 5,584,086 | 12/1996 | Van Winkle et al. ........................ 5/644 |

Primary Examiner—Michael Peffley
Assistant Examiner—Roy Gibson
Attorney, Agent, or Firm—R. William Graham

[57] ABSTRACT

The present invention relates to an equine therapeutic device which includes a thermal magnetic field transfer member which configured to conform about a horse's leg.

8 Claims, 3 Drawing Sheets

EQUINE THERAPEUTIC DEVICE

This is a continuation in part of copending U.S. Ser. No. 08/870,226 filed Jun. 06 1997.

BACKGROUND OF THE INVENTION

1. Field of the Invention

The present invention relates to a thermal magnetic controlled device. More particularly, the present invention relates to a thermal magnetic transfer device which is configured to conform about a part of a body, for example a horse's leg.

2. Related Art

The use of thermal transfer devices in the field of therapeutically treating humans by way of such devices is known to exist. Some of such devices include a heat transfer element, a thermal fluid bath and a pump for circulating the fluid through the element. The transfer element includes a generally hollow pad having an inlet and outlet through which fluid flows.

There exist a number of wraps which exist in the equine area for aiding in therapy of horses. These types of wraps are designed to support the horse's leg to bandage an open wound. Some of these devices are cotton or similar cloth material wraps which supportively aid the horse's condition. However, there has yet to be a device which thermally treats the horse's leg to effect a therapeutic result.

There have been other therapeutic means for treating humans and animals. Particularly, magnetic therapy treatment has been employed in the treatment of arthritis, wrinkles, discolored, blotchy pigmentation or unhealthy complexion of the skin. The exact mechanism by which the treatment derives its efficiency is not exactly known, but appears to be in part linked to the formation of collagen during magnetic therapy treatment. The fact that pulsed magnetic field can stimulate collagen and proteoglycan synthesis by connective tissue cells is documented. Massage therapy has been known to relieve muscle pains by improving blood circulation. Similarly, magnetic therapy has been shown to benefit the circulation of blood in humans and in animals.

One device known provides magnetic therapy, using magnetic field lines which cross a subject's skin and is applied to the tissues underlying the skin being massaged. Other devices contemplate using electromagnetic devices for treating living tissues and organs. These devices are typically left attached to a limb or the torso. Still others contemplate using permanently magnetized pads and sheets to treat humans or animals. These devices typically have a flexible sheet impregnated with magnetic ferrite particles in various patterns. In addition to physical training, magnetic therapy can be used to condition, promote healing of those overworked muscles, and keep animals in peak condition.

There remains a need to improve therapy and treatment of human and animal tissue, such as an injury to a horse's leg. There remains a need for a therapeutic device which is particularly well suited for providing therapeutic treatment of human and animal body tissue, such as a horse's leg. The present invention fulfills these needs.

BRIEF SUMMARY OF THE INVENTION

It is an object to improve the device for treating a horse's leg.

It is another object to provide unique thermal magnetic transfer device suitable for use on a human or animal, such as a horse's leg.

Accordingly, the present invention is directed to a thermal magnetic transfer device having a first relatively flexible member which is thermally conductive and permits magnetic field migration therethrough configured to fit about a part of a tissue of a body, such as a horse's leg and a second relatively flexible member of a complimentary configuration to the first member, wherein the first and second members are disposed adjacent one another and are peripherally sealingly connected along outer edges.

An inlet is formed on a first side of the region and an outlet is formed on a second side of the region such that when fluid flow is introduced into the device through the element via the inlet there is a flow pattern created which moves from the first side through to the second side an out the outlet. A magnetic member is operably disposed between the first and second relatively flexible members such that when the fluid flow is introduced, a magnetic field is created in the fluid. The first and second members are also sealingly connected along an internal line extending inwardly from a predetermined region of the edges to aid direction flow of the fluid.

A third relatively flexible member of a complimentary configuration to the second member is removably connectable thereto and includes at least one member connected to the third relatively flexible retaining member for fastening one end of the third relatively flexible member to another end of the third relatively flexible member.

Preferably, VELCRO hook and loop fastener members releasably interconnect the second relatively flexible member the third relatively. Also preferably, a plurality of VELCRO hook and loop fastener members serve as the fasteners which interconnect the ends of the third relatively flexible member.

Other objects and advantages will be readily apparent to those skilled in the art upon viewing the drawings and reading the detailed description hereafter.

DETAILED DESCRIPTION OF THE INVENTION

Figure 1:
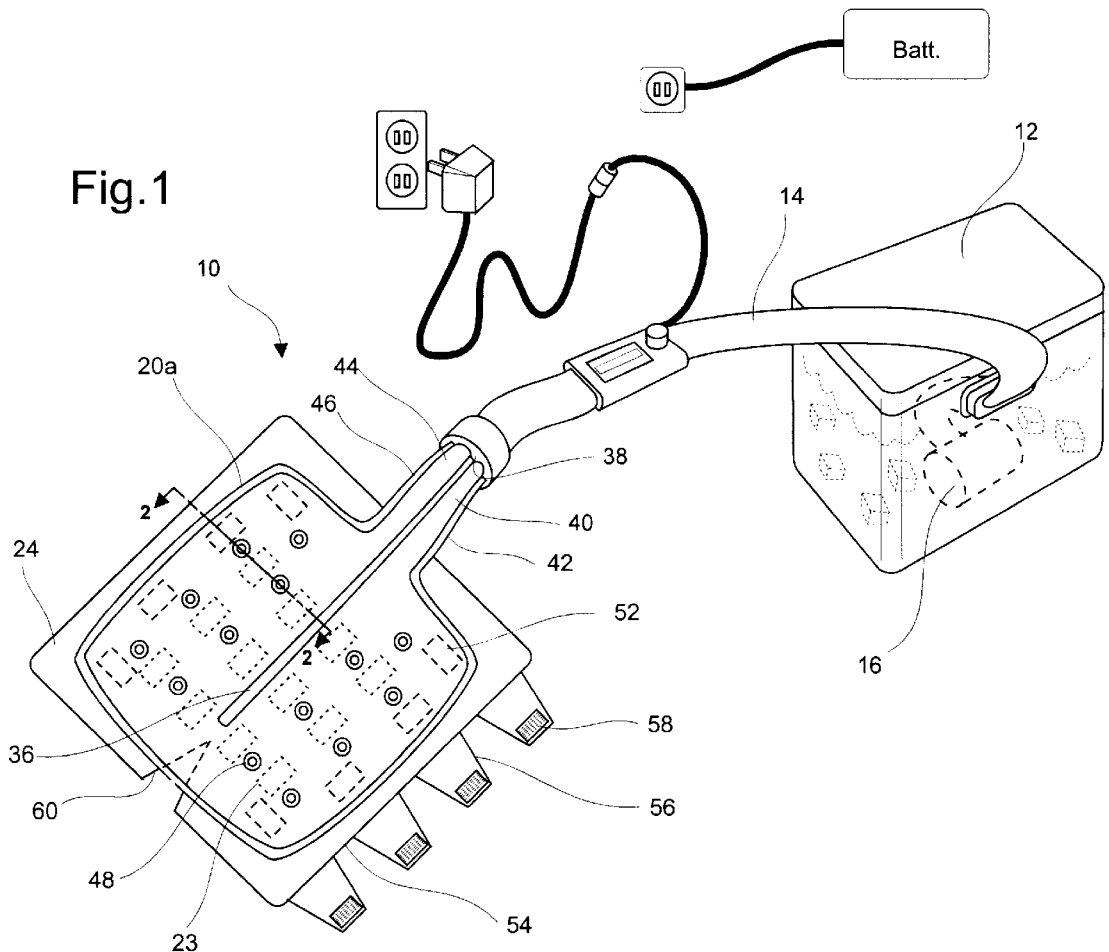
FIG. 1 is a perspective view of one embodiment of the present invention.

Referring now to the drawings, the thermal magnetic transfer device of the present invention is generally referred to with the number 10. The device 10 of the present invention is operably connectable to a thermal bath 12 by way of a two-way feed and return thermally controllable line 14 which is operably connected to a pump 16. The bath 12, line 14 and pump 16 can be of the type shown in U.S. Pat.

No. 5,507,792 which are incorporated herein by reference. In one embodiment, the pump 12 is powered by a d.c. current.

Figure 2:
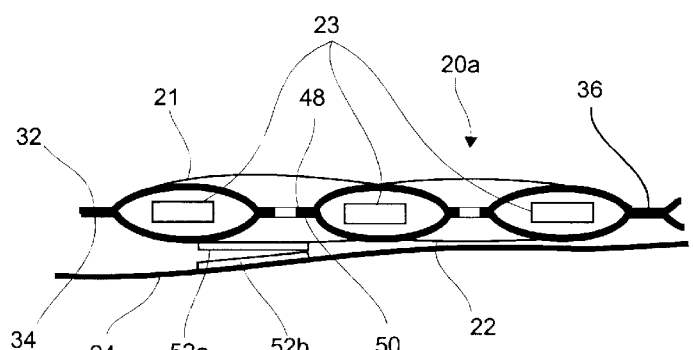
FIG. 2 is a cross-section of a part of the device in FIG. 1 along line 2—2.
Figure 3:
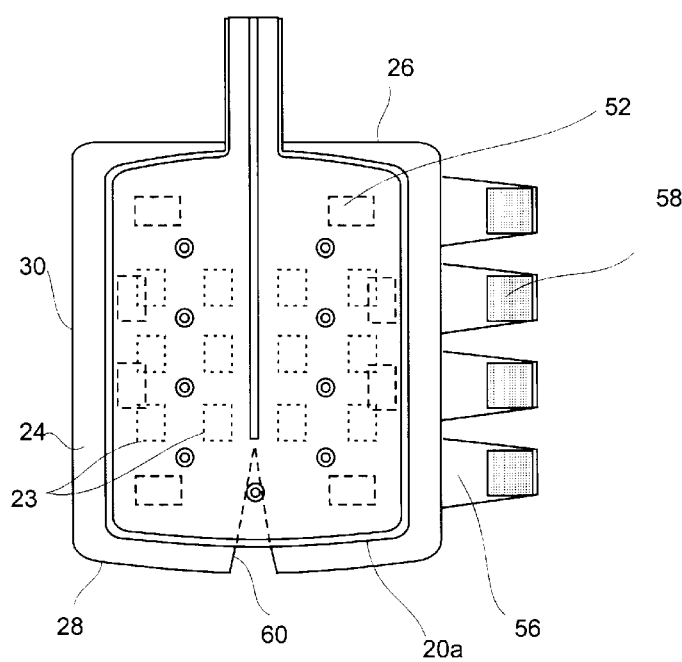
FIG. 3 is a plan elevational view of a part of the device in FIG. 1.
Figure 4:
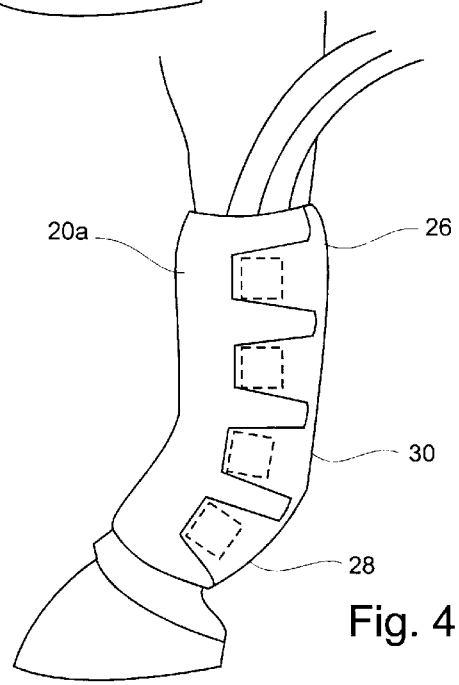
FIG. 4 is a view of the part of the device shown in FIG. 3 in use.

As shown herein, the device 10 is particularly designed to be configured to fit to a horses leg and includes use of one of three thermally conductive members 20a, 20b or 20c. However, the invention is not to be limited to these particular design applications and can take on a variety of other configurations which utilize the underlying features of the invention described herein. As seen in FIGS. 1–3, the thermally conductive member 20a has first and second relatively flexible thermally conductive members 21 and 22 and a relatively flexible retaining member 24 shaped to conform to the lower leg of the horse. The thermally conductive member 20a has an upper end 26 for disposition above the leg's fetlock and a lower end 28 for disposition below the leg's pastern and an intermediate portion 30 configured to conform and receive the fetlock of the leg.

The first and second relatively flexible thermally conductive members 21 and 22 are of a complimentary configuration and may be of any suitable plastic material, such as a polymer made of polyethylene or polyurethane. The first member 21 and second member 22 are disposed adjacent one another and are peripherally sealingly connected along outer edges 32 and 34, respectively. The first member 21 and second member 22 are also sealingly connected along a internal line 36 from a predetermined region 38 of the edges 32 and 34 and extends inwardly therefrom as shown in FIG. 1.

An inlet 40 is formed on a first side 42 of the region 38 and an outlet 44 is formed on a second side 46 of the region 38. The inlet 40 and outlet 44 are operably connected to the line 14 such that when fluid flow is introduced from the bath 12 into the device 10 via the line 14 and inlet 40 there is a flow pattern created which moves from the first side 42 through to the second side 46.

There also exists a plurality of internal circular connections 48 and 50 which are spaced of from each other throughout the member 20a. These connections 48 and 50 restrict and divert the flow path of the fluid.

Operably disposed within and between the first member 21 and second member 22 are a plurality of magnetic members 23. These magnetic members 23 are preferably disposed in a relatively spatially fixed position with respect to one another by means of gluing, adhesion or by virtue of the magnetic members 23 being of a sufficiently large size to provide for only limited movement between the connections 48 and 50. The particular size and shape of the magnetic members 23 will act to enhance or detract from a magnetic field which is formed.

The fluid 25 referred to herein is preferably of a readily polarizable type, such that positive and negative ions may actively migrate within the fluid in accordance with a magnetic field 27 which is defined by the magnetic members 23 between the members 21 and 22. Water, for example, can be one type of fluid suitable for use in the present invention.

Spatially positioned and connected to an outer surface of the second member 22 are a plurality of VELCRO hook and loop fastener members 52 which are fixedly connected thereto, i.e., the members 52 are glued to the surface. The VELCRO hook and loop fastener members 52 each include a hook member 52a and loop member 52b, wherein hook member 52a is glued to second member 22.

The relatively flexible retaining member 24 is configured to substantially envelop the members 21 and 22 when connected to the horse's leg as shown in FIG. 3. The relatively flexible retaining member 24 can be made of a cloth or synthetic material and has VELCRO hook and loop fastener members 52b connected thereto via glue or stitching and are arranged spatially from one another in a complimentary manner to readily permit secure attachment of the member 22 thereto. Extending from one side 54 of the member 24 are a plurality of fastening members 56 which include VELCRO hook and loop fastener member 58 connected thereto, i.e., the VELCRO hook and loop fastener member 58 is stitched for example to the fastening member 56. The member 24 includes an outer surface, preferably made of neoprene material or the like, to which the Velcro members 58 releasably connect. By so providing, the flexible retaining member 24 can wrap about the members 21 and 22 and hold the same along with itself in a self supporting manner on the horse's leg. A relief or notched V-portion 60 is defined in the end 28 to permit the retainer member 24 to be conformingly wrapped about the horses leg.

Figure 5:
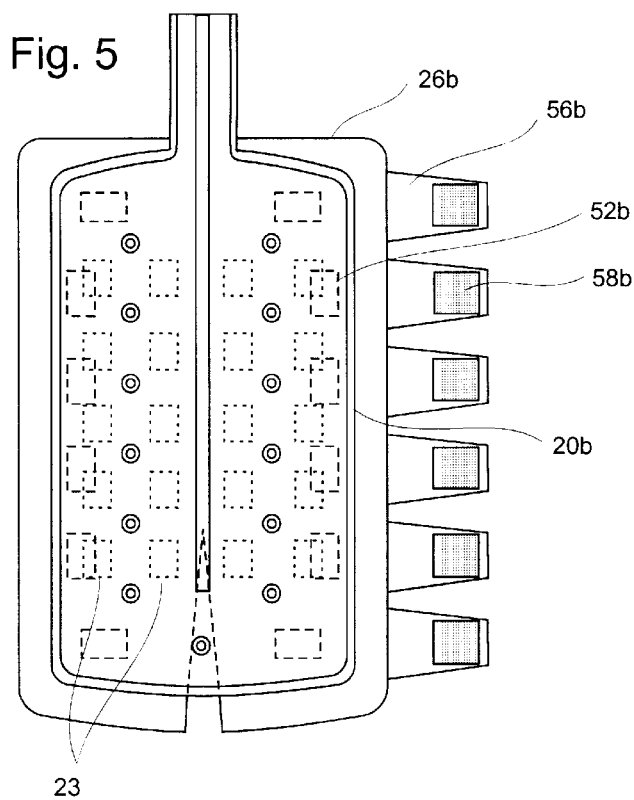
FIG. 5 is a plan elevational view of a part of the device in FIG. 1.
Figure 6:
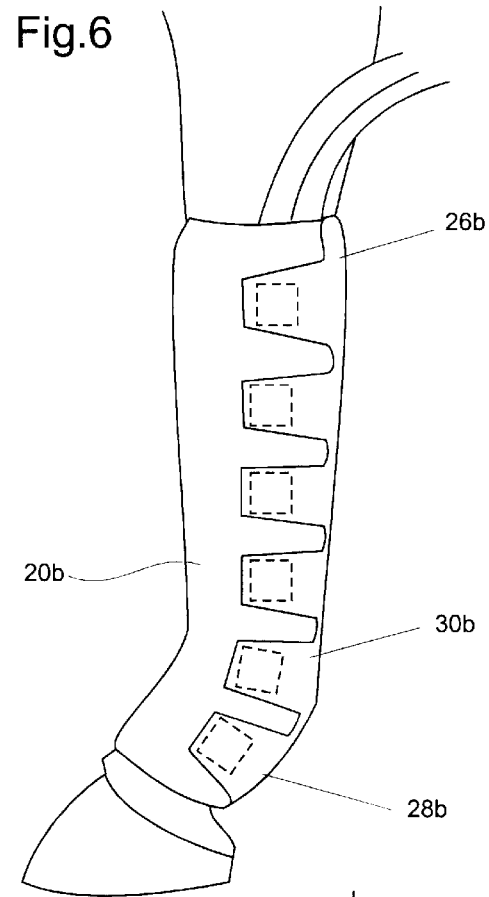
FIG. 6 is a view of the part of the device shown in FIG. 5 in use.

FIGS. 5 and 6 show the thermally conductive member 20b substantially similar to that shown in FIGS. 1–3. Here, the end 26b extends sufficiently beyond the fetlock to substantially cover the cannon bone of a horse's leg. There are additional fastening members 56b for providing fastening about this area.

Figure 7:
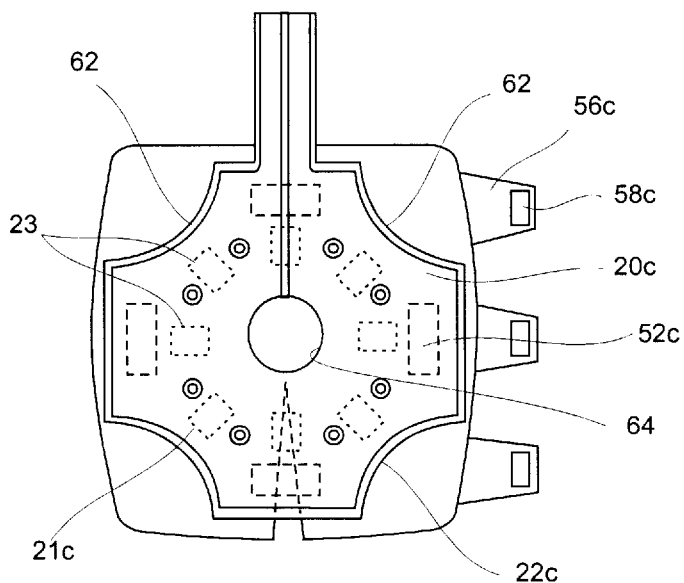
FIG. 7 is a plan elevational view of a part of the device in FIG. 1.
Figure 8:
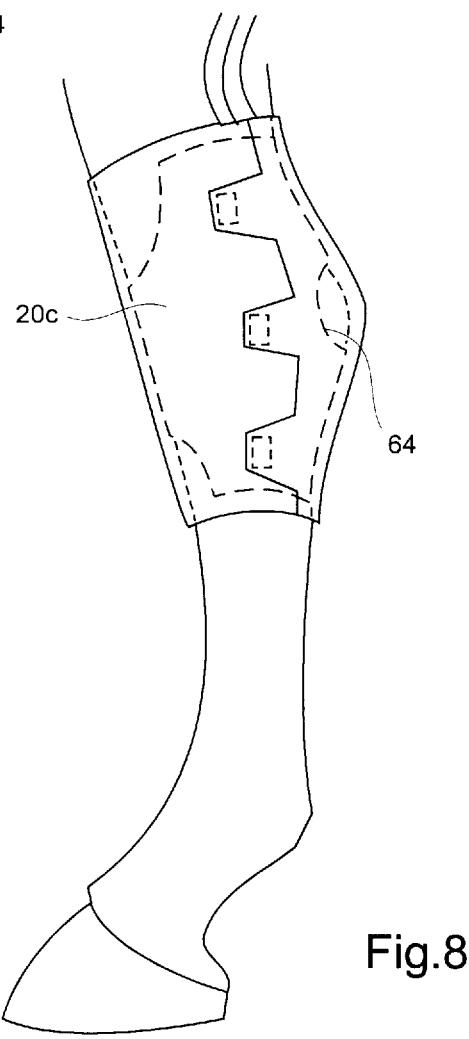
FIG. 8 is a view of the part of the device shown in FIG. 7 in use.

In FIGS. 7 and 8, the thermally conductive member 20c is shown which is designed for application to a hawk bone of the horse's leg. Here, the structure is not too unlike that previously described for the flexible thermally conductive members 21 and 22, with the exception cut-away corner portions 62 and cut-away center portion 64 of the flexible thermally conductive members 21c and 22c and the spatial connective positioning of the VELCRO hook and loop fastener fasteners 56c. As seen in FIG. 8, the thermally conductive member 20c is easily positioned about the Hawk by disposing the cut-away center portion 64 adjacent the joint.

The above described embodiments are set forth by way of example and are not for the purpose of limiting the present invention. It will be readily apparent to those skilled in the art that obvious modifications, derivations and variations can be made to the embodiments without departing from the scope of the invention. Accordingly, the claims appended hereto should be read in their full scope including any such modifications, derivations and variations.

What is claimed is:

1. A thermal and magnetic transfer device for receiving a therapeutic fluid, which includes:

a first relatively flexible member which is thermally conductive and permits magnetic field migration therethrough and configured to fit about a part of a body and having a continuous peripheral outer edge;

a second relatively flexible member of a complimentary configuration to said first member and having a continuous peripheral outer edge, wherein said first member and said second member are disposed adjacent one another and are peripherally sealingly connected along said outer edges to form a sealed edge;

an inlet formed along said sealed edge;

an outlet formed along said sealed edge;

a magnetic member operably disposed between said first relatively flexible member and said second relatively flexible member; and a polarized and thermally conductive fluid flowing into said inlet in contact with said magnetic member and out said outlet, wherein polarization occurs through said contact.

2. The device of claim 1, wherein said first member and second member are sealingly connected along an internal line which extends inwardly from a predetermined region of said sealed edge between said inlet and said outlet.

3. The device of claim 2, wherein when said fluid is introduced into said device through said inlet there is a thermal magnetic field flow pattern created which moves from said inlet on a first side through to a second side and out through said outlet of said device.

4. The device of claim 1, which further includes means for releasably interconnecting a first side of said device and a second side of said device in a manner to retain said device about the part of the body.

5. The device of claim 1, wherein said first member and said second member include a relief portion defined therein.

6. The device of claim 1, wherein said first member and said second member are generally rectangular and each has a V-shaped cut out surface portion extending inwardly from said outer edges.

7. The device of claim 4, wherein said releasably interconnecting means includes a relatively flexible retaining member releasably connectable to one of said first relatively flexible thermally conductive member and said second relatively flexible thermally conductive member and having means for releasably wrapping about said first relatively flexible thermally conductive member and said second relatively flexible thermally conductive member and the part of the body in a self-supporting manner.

8. The device of claim 7, wherein said releasable wrapping means includes hook and loop fasteners interconnecting one side of the relatively flexible retaining member to another side of the relatively flexible retaining member.

* * * * *